United States Patent [19]

Poole et al.

[11] Patent Number: 4,596,142
[45] Date of Patent: Jun. 24, 1986

[54] ULTRASONIC RESONANCE FOR DETECTING CHANGES IN ELASTIC PROPERTIES

[75] Inventors: Michael J. Poole, Abingdon; John P. Charlesworth, Witney, both of England

[73] Assignee: United Kingdom Atomic Energy Authority, London, England

[21] Appl. No.: 626,725

[22] Filed: Jul. 2, 1984

[30] Foreign Application Priority Data

Jul. 8, 1983 [GB] United Kingdom ............... 8318606

[51] Int. Cl.$^4$ ............................................. G01N 29/00
[52] U.S. Cl. .............................................. 73/579; 73/86
[58] Field of Search ................ 73/610, 611, 613, 614, 73/615, 631, 609, 579, 86, 599; 422/53

[56] References Cited

U.S. PATENT DOCUMENTS

| | | | |
|---|---|---|---|
| 3,056,284 | 10/1962 | Marsh et al. | 73/599 |
| 3,379,051 | 4/1968 | Zeutschel et al. | 73/614 |
| 3,538,753 | 11/1970 | Gericke | 73/614 |
| 3,554,015 | 1/1971 | Brech | 73/614 |
| 3,914,987 | 10/1975 | Bickel et al. | 73/610 |
| 3,946,600 | 3/1976 | Rettig et al. | 73/590 |
| 4,126,048 | 11/1978 | Mansson | 73/611 |
| 4,169,385 | 10/1979 | Kellogg et al. | 73/610 |
| 4,475,395 | 10/1984 | Flax | 73/631 |

FOREIGN PATENT DOCUMENTS 2002902 2/1979 United Kingdom .

Primary Examiner—Stephen A. Kreitman
Attorney, Agent, or Firm—William R. Hinds

[57] ABSTRACT

Some forms of corrosion, and inter-granular attack in particular, occur without significantly altering the bulk dimensions of the body attacked. Where elastic properties are changed, this is detected by a sensitive ultrasonic inspection based upon the resonant frequency or frequencies with which the ultrasonic signals reverberate within the body. Resolution is improved by gating out the first, top, surface reflection and by swept gain control through the gating period.

1 Claim, 24 Drawing Figures

ULTRASONIC RESONANCE FOR DETECTING CHANGES IN ELASTIC PROPERTIES

The invention relates to a method and apparatus for detecting changes in elastic properties of a body, in particular for discovering presence of intergranular attack or other forms of corrosion which do not alter significantly the bulk dimensions of the body.

Inter-granular attack is a form of corrosion in which the attack is confined to the grain boundaries. In an extreme case, this will result in the grains becoming completely unbonded from each other but, in less severe cases, they may be bonded over part of their contact area. In most circumstances the attacked region forms a layer of uniform thickness but sometimes there are small regions where the attack has penetrated much further than elsewhere. These regions of deep attack are known as 'fingers' and may result from the growth of intergranular attack from pre-existing stress corrosion cracks, although this is not certain.

Inter-granular attack is known to occur in some circumstances on, for example, the outer surface of steam generator tubes in a tube-in-shell heat exchanger made from Inconel 600. The attack occurs at or near the region where the tubes emerge from the tube sheet. The growth of intergranular attack through a substantial proportion of the tube thickness could lead to a tube burst, especially in fault conditions of the type where the primary/secondary pressure differential is increased (e.g. steam-line break). Even if the uniform layer intergranular attack was no threat to the tube integrity, fingers of intergranular attack could lead to leakage.

The invention arises from the appreciation that a layer of intergranular attack, which, in the form of a uniform layer, is considered most difficult to detect, changes the elastic properties of the material and, provided with apparatus of sufficient sensitivity, it is possible to detect the changes ultrasonically.

The problem is discussed in an article entitled "Ultrasonic Inspection of Stainless Steels for Intergranular Corrosion" by V. N. Prickhod'ko in Industrial Laboratory translated from Zavodskaya Laboratoriya, Vol 43, No. 5, May, 1977. Reference is made to the requirement for high sensitivity to small changes in the velocity of ultrasonic waves in the test metal.

An object of the present invention is to provide a method and attendant appparatus for carrying out the method in which the required sensitivity is achieved in a way in which results can be satisfactorily related to the changes in properties under investigation.

Accordingly, the invention provides a method for detection in a component having thin walls such as a heat exchanger tube of intergranular attack or other forms of corrosion which do not alter significantly the thickness of the said walls, which method comprises injecting ultrasonic elastic wave signals into the walls of the component at a selected plurality of identified locations before the component has been exposed in use to intergranular attack or other corrosion as aforesaid and recording for each location data representative of the resonant frequency with which the signals reverberate across the thickness of the thin walls, injecting ultrasonic elastic wave signals into the component at a selected plurality of locations after the component has been exposed in use to intergranular attack or corrosion as aforesaid, and comparing at each location the resonant frequency with which the signals reverberate within the component with a resonant frequency computed from the recorded data to be that expected for the respective location in the absence of intergranular attack or corrosion.

There is also provided herein apparatus for detecting change in elastic properties of a body capable of transmitting ultrasonic signals and having a configuration providing reflecting surfaces whereby defined resonance of ultrasonic signals within the body can occur, which apparatus comprises a transducer source of ultrasonic elastic wave pulses and means for injecting the pulses into the body, a transducer receiver (which may be the same transducer as the source) for converting ultrasonic elastic wave signals received from the body into corresponding electrical signals, gating means for passing for a predetermined period electrical signals corresponding to resonance response signals received from the body following injection of a pulse from the said source, and frequency analyser means for performing frequency analysis of the resonance signals passed by the gating means.

Preferably the transducer receiver is connected via an amplifier to a zero-crossover detector and a delay, the zero-crossover detector establishing an accurate time reference at the commencement of the reflected signals received from the body and the delay controlling the said gating means so as to gate out most of the reflection from the surface of the body closest to the transducer source and initiate passage of resonance response signals to the frequency analyser.

Preferably the apparatus includes means for providing a swept increase in amplification of the signals passed to the frequency analyser means, the sweep function being chosen to compensate for the attenuation with time in the signals received during the gating period when the signals are passed to the frequency analyser means.

Specific constructions of apparatus and a method embodying the invention will now be described by way of example and with reference to the drawings filed herewith, in which.

Figure 1:
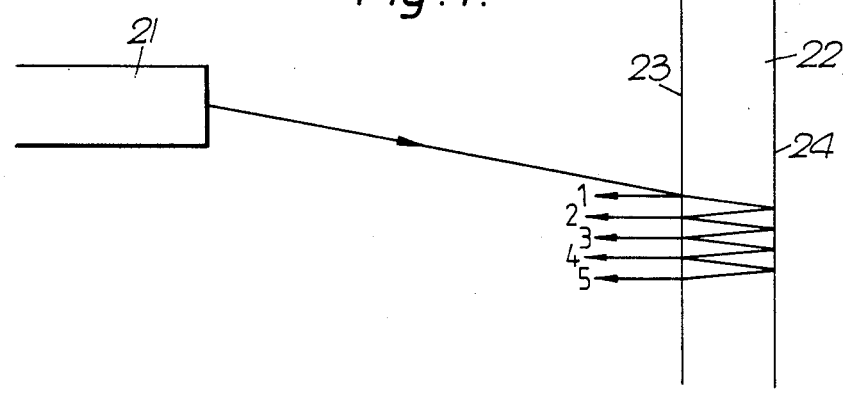
FIG. 1 illustrates diagrammatically the form of ultrasonic reflections from a sample.

Samples in the form of plates or tubes will provide thickness mode resonant frequencies which derive from reflections at the opposed surfaces. This is illustrated in FIG. 1.

If the beam from a wide-band (i.e. short pulse) transducer 21 is directed normally at a piece of material 22 having parallel faces 23, 24 (at least over the beam width) the reflected sound will be the sum of reflection (1) from the outer surface 23 and reflections (2), (3) etc. caused by multiple reflections inside the material. Each beam will differ in phase by $2\pi 2t/\lambda$ from the preceding one (a situation analogous to the Fabry-Perot etalon in optics) and the addition of these beams leads to sharp dips in the reflected intensity at frequencies for which the material thickness equals $n.\lambda/2$, where n is any integer. Thus if the pulse echo is subjected to frequency analysis the position of these resonances gives information about effective plate thickness and effective sound velocity, while the breadth and intensity of the resonances is determined inter alia by absorption and scattering of the sound in the material.

Signal legibility is significantly improved by eliminating most of the first reflection (1) from the sum. Under these conditions the reflected spectrum becomes the same as the transmitted spectrum and consists of a series of peaks at frequencies given by:

$$f_R = nV/2t$$

where V is the sound velocity and t the thickness.

The use of the reflected, rather than the transmitted, signal is dictated by the need for the apparatus to have the capability for examining tubes without access to the outside of the tube. Although apparatus for examining tubes by transmission suitable for laboratory use could be devised, a reflection system is considered necessary for inspection of steam generator tubes in situ.

Most of the first reflection (1) is eliminated in this example by using a pulsed transducer and a time gate in the detector circuit set to open sufficiently long after the arrival of the first reflection (1) for its intensity to have died away to an insignificant level. This is illustrated in FIG. 2 in which is represented each of the reflections 1, 2, 3, 4, 5, the gate, and the resultant signal RS passed by the gate.

Figure 2:
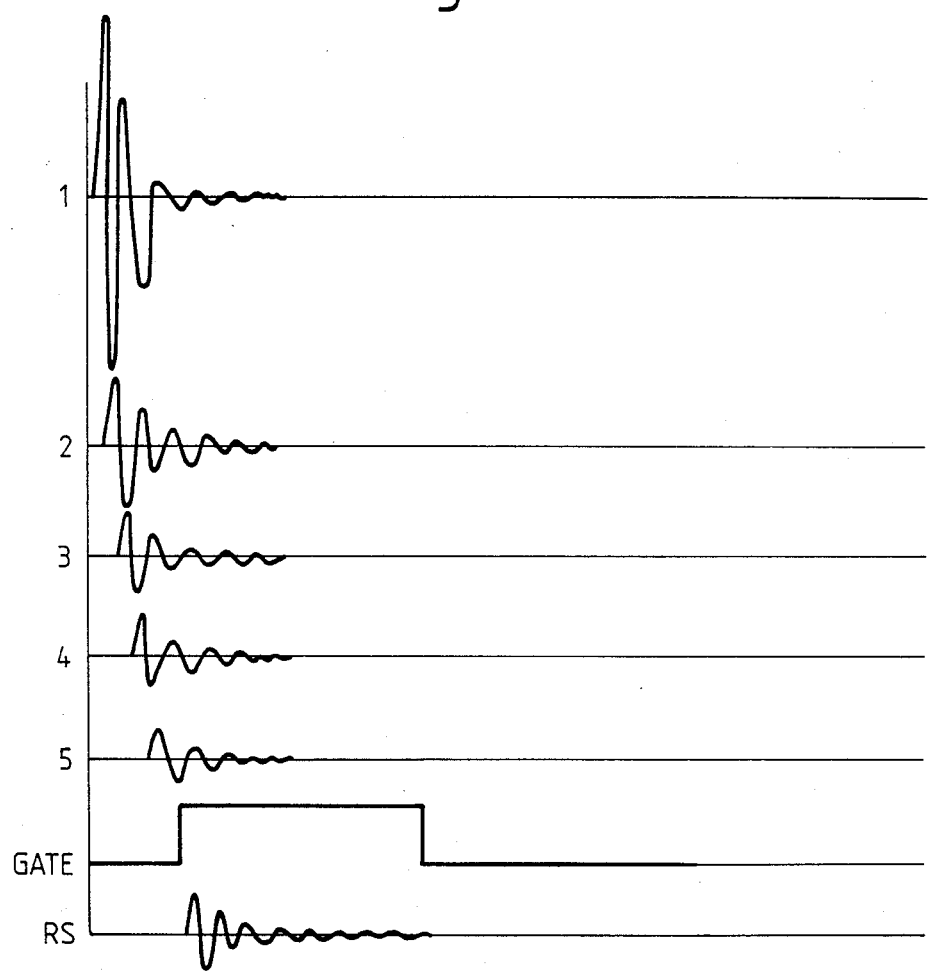
FIG. 2 illustrates with reference to the reflections shown in FIG. 1 the gating principle employed.

As indicated in FIG. 2, the intensity of the successive reflections progressively decreases owing to attenuation in the material 22.

The operation may be compared with striking a bell, eliminating the first loud sound and listening to the ensuing resonant hum of the bell.

A further improvement in resolution is achieved by passing the signal through an amplifier with time-dependent gain. The sharpness of the frequency peaks depends on the width of the gate. However, as the intensity of the signal progressively decreases, so it has progressively less effect on the shape of the spectrum observed. By increasing the gain of the amplifier after the gate is opened so that the attenuation of the signal is at least approximately compensated, the useful width of the gate that can be used is limited only by the signal to noise ratio of the incoming signal. By this means maximum information can be extracted from the signal. Accordingly, the duration of the time gate is chosen to be sufficiently long to admit all of the signal having a useful intensity above noise.

Figure 3:
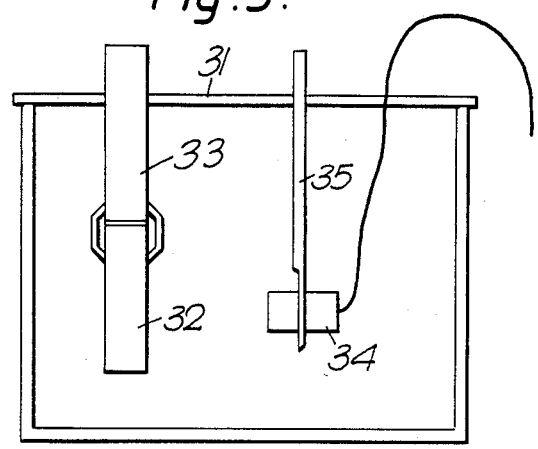
FIG. 3 is a diagrammatic representation of an apparatus.

The apparatus is illustrated in FIG. 3. A standard water tank 31 is used with the test sample (tube or plate) 32 mounted in clamp 33. Transducer 34 mounted in clamp 35 is adjustable in angle about two planes respectively containing and transverse to the longitudinal axis of the sample 32. The transducer 34 is driven by a conventional transducer driver (not illustrated) and the received signal processed by the components represented in FIG. 5, the operation of which is described below.

Figure 4:
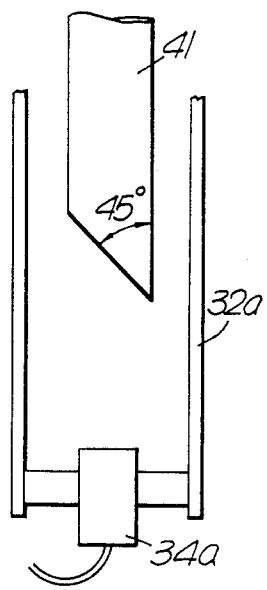
FIG. 4 is a diagrammatic representation of a modified arrangement.

FIG. 4 illustrates a modified arrangement for effecting inspection from inside a sample tube 32a. Transducer 34a is mounted at one end of the tube 32a aligned with the tube axis. At the other end and also aligned with the tube axis is a steel rod 41 machined to 45° at the end. In an example the sample tube 32a had an internal bore of 15 mm diameter and the rod 41 had a diameter of 13 mm.

Figure 5:
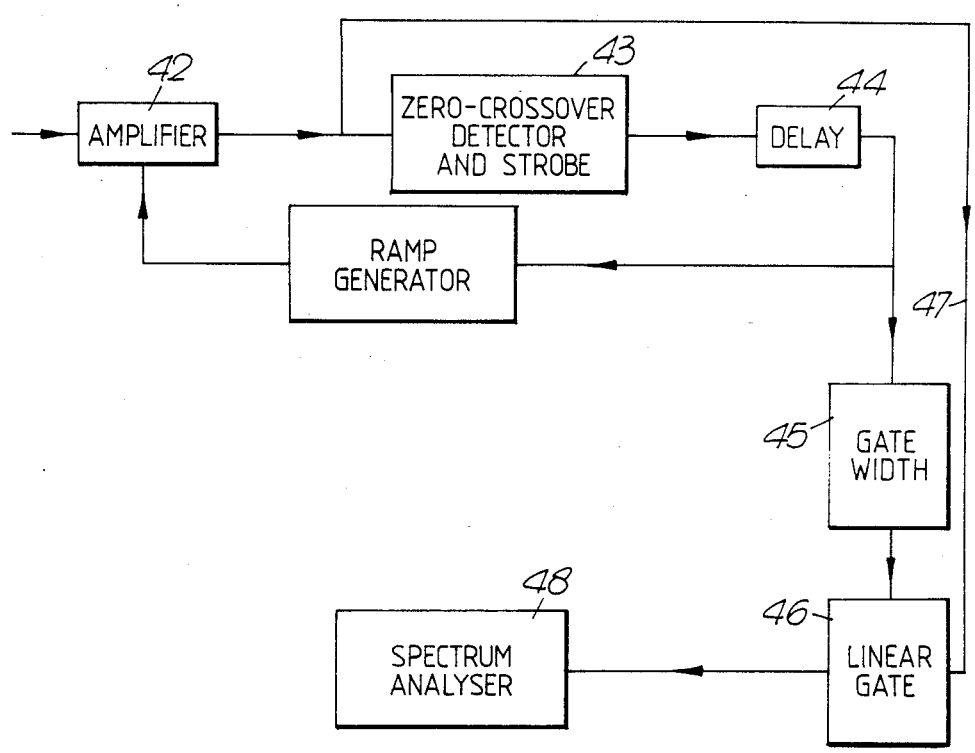
FIG. 5 is a block electrical circuit diagram.

Referring to FIG. 5, received reflected signals from the transducer 34 or 34a are passed to a wide band amplifier 42. The arrival of the reflected signal pulse is detected, an accurate time reference is established at the first negative going zero-crossing after threshold detection, and a coincident strobe pulse is generated by unit 43 labelled ZERO-CROSSOVER DETECTOR AND STROBE. Delay 44 is set so as to eliminate most of the signal from the front surface 23 (signal 1 in FIG. 2) and a timing unit 45 labelled GATE WIDTH opens linear gate 46 for a predetermined period set to include the desired duration of the remaining signal as described above. Output from the delay 44 also triggers ramp generator 49 to sweep the gain of amplifier 42.

The signal from the amplifier 42 on line 47 passed by the linear gate 46 is fed to a spectrum analyser 48.

FIGS. 6 to 13 are drawings representing the display on a cathode ray oscilloscope driven by the spectrum analyser 48.

FIGS. 6 to 9 illustrate the principles of the method and were obtained using a sample of 1/16th inch (1.5 mm) thick mild steel plate.

Figure 6:
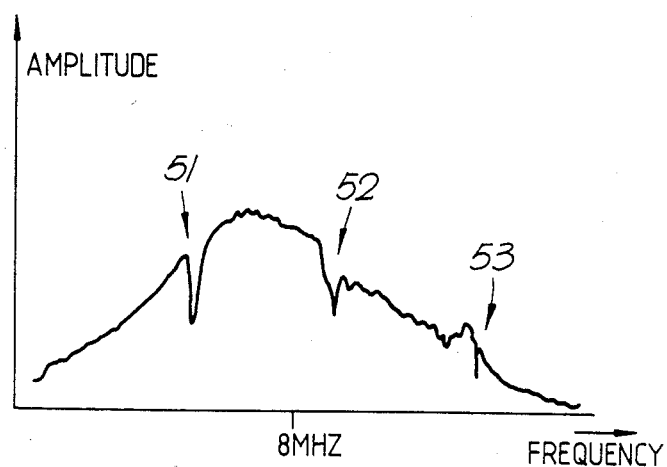
FIGS. 6 to 13 show representations of frequency spectrum analysis of various test samples.

FIG. 6 shows the resonant dips at 51, 52, 53 obtained by analysing the entire unprocessed signal.

Figure 7:
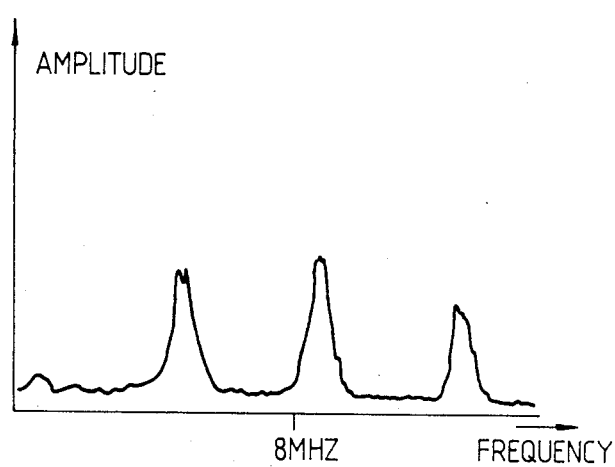

FIG. 7 shows the effect of gating out the initial part of the reflected signal pulse (1 in FIG. 2).

Figure 8:
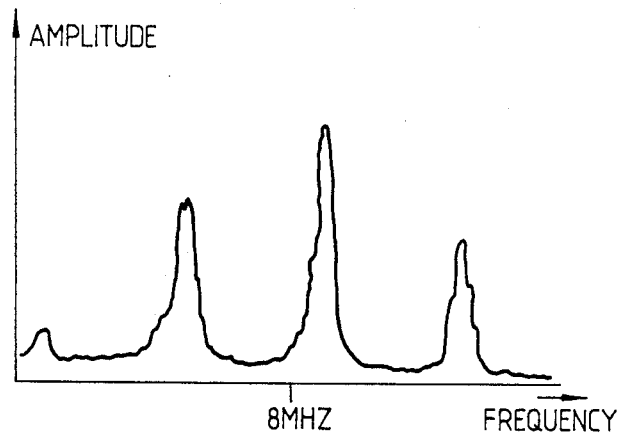

FIG. 8 shows the improvement in resolution achieved by sweeping the amplifier gain so as to compensate for signal attenuation during the period for which the gate 45 is open.

Figure 9:
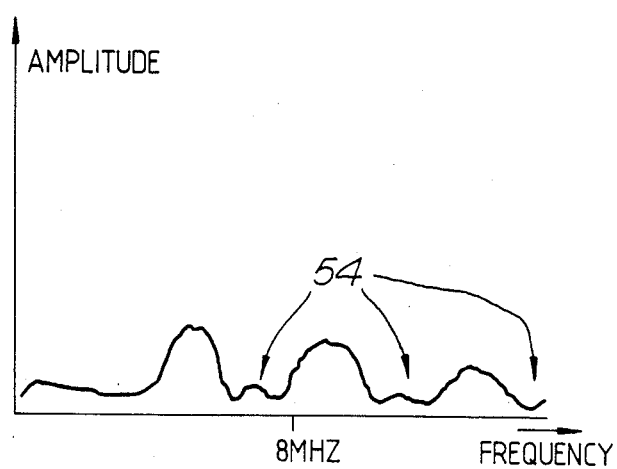

FIG. 9 shows the effect of shortening too much the duration of the linear gate 46. An interesting effect, in addition to the loss of resolution of the resonance peaks, is the appearance of 'side lobes' at 54. If the gate admits n cycles of the fundamental resonance then there are n−2 side lobes. In this respect the effect of the gate is exactly analogous to the total width of a grating in diffraction of light at a grating.

An alternative treatment of the reflection (or transmission) by a thin plate is to look upon it as a filter superposing its response on the frequency spectrum of the transducer. The intensities of the various peaks are dependent not only on the plate resonances but also on the amount of energy at the resonant frequencies in the initial signal. It is thus important to choose a transducer having a spectrum wide enough to cover all the resonances of interest. Alternatively by choosing a narrow band transducer the response can be restricted to a few resonances.

FIGS. 10 to 12 illustrate results of inspection at various parts of various samples, in each case with the apparatus operating in the mode illustrated in FIG. 8.

All the samples were Inconel 600 and were either in the form of a sheet 2"×6"×1 mm thick (nominal) or tubes 15 mm ID×1 mm wall thickness. Intergranular attack had been induced to grow in the samples by a variety of methods and to a variety of depths, usually only over a part of the surface available so as to leave an uncorroded area for reference.

All samples were nominally 1 mm thick and had a fundamental resonant frequency of ~3 MHz. Inspection frequencies were therefore 3n MHz where the values of n available depended on the particular transducer in use.

Figure 10A:
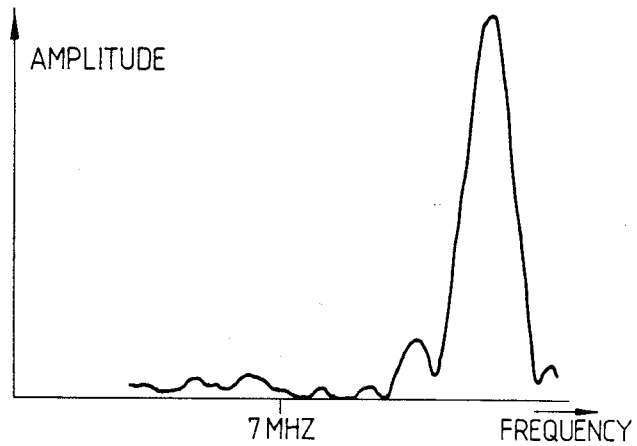
Figure 10B:
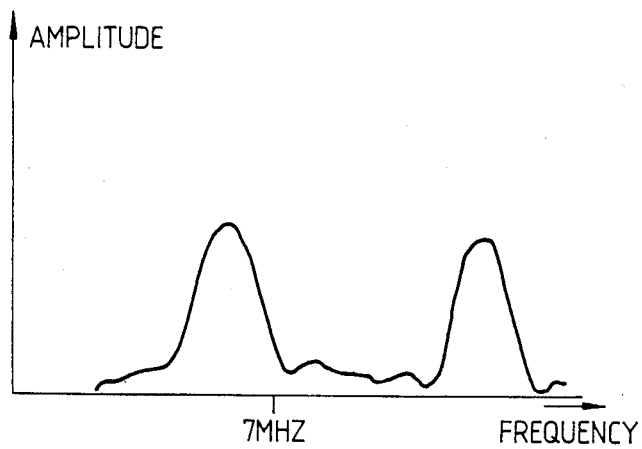
Figure 10C:
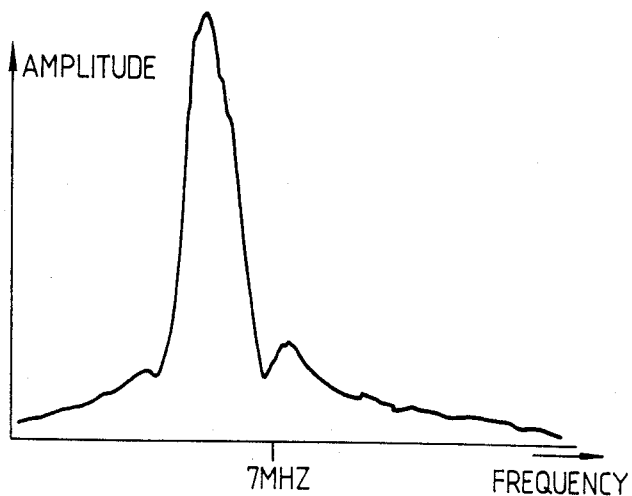

FIG. 10 shows results from a sheet treated over a limited region with potassium tetrathionate to produce intergranular attack to a nominal depth of 25% of the thickness of the sheet. Using the 9 MHz resonance a shift of −400 kHz− i.e. 4.4% was observed in passing from the clean (FIG. 10a) to the corroded (FIG. 10c) sections. This corresponds to a decrease in the ultrasonic velocity in the intergranular attack (increase in thickness was ruled out by micrometer measurements). There was no sign of an increased frequency peak due to reflection at the interface between the IGA and unattacked metal.

A broad beam transducer was used and it is interesting to note that at the junction between the corroded and clean areas both peaks are clearly visible (FIG. 10b), demonstrating the possibility of seeing what fraction of the area is attacked.

Figure 11A:
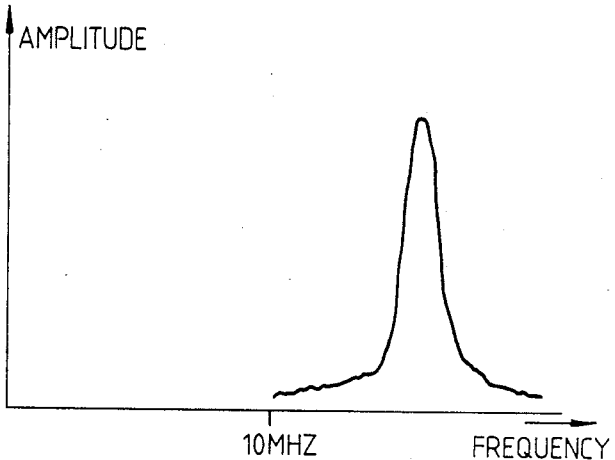
Figure 11B:
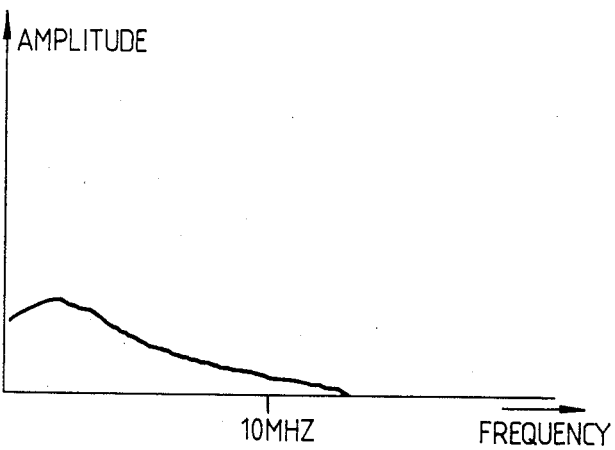

FIG. 11 shows results from a tube having regions of intergranular attack to a nominal depth of 12–15% of the wall thickness induced by treatment with nitric acid. Observations were made initially at the 9 MHz resonance. A frequency shift of 1.3 MHz (14.4%) and a distinct broadening of the peak was observed between the clean (FIG. 11a) and attacked (FIG. 11b) regions. This broadening is in distinct contrast to the effect observed on the sheet sample (FIG. 10) and illustrates the different behaviour of samples prepared by different routes. This difference is confirmed by the much greater frequency shift (14.4% for 12–15% intergranular attack as against 4.4% for ~25% intergranular attack) in this sample.

Figure 12A:
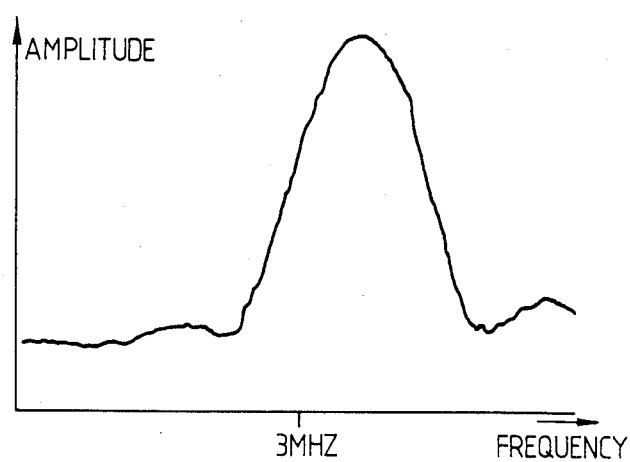
Figure 12B:
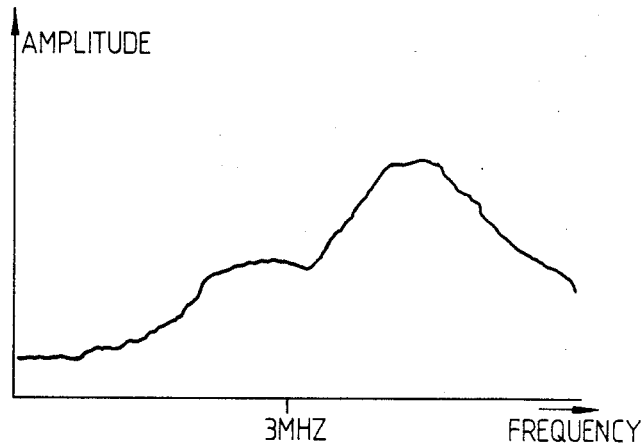

FIG. 12 shows the results of a further observation made at the 3 MHz peak. FIG. 12a shows the response from an unattacked region. On entering the attacked region (FIG. 12b) the peak splits into two, one of which moves up and the other down in frequency. The higher frequency component is interpreted as being due to reflection at the intergranular attack interface and the lower as due to the reduced velocity in the intergranular attack region. The relative movements are ~3% up and ~4.5% down. No explanation is yet available why these figures are so much less than either the intergranular attack depth or the frequency shift observed at 9 MHz, although as regards the latter it is not unreasonable to suppose that the velocity may be frequency dependent.

Figure 13A:
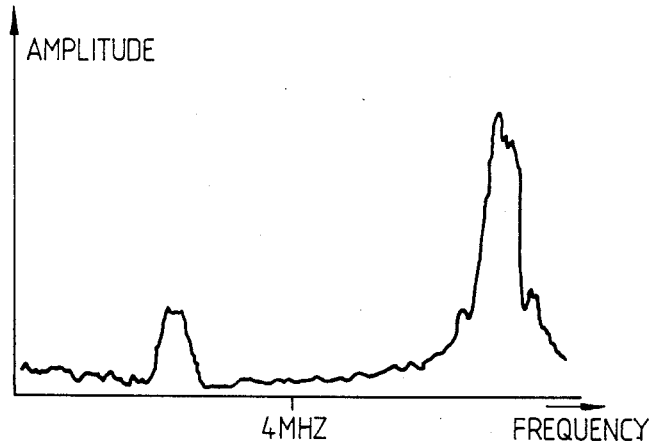
Figure 13B:
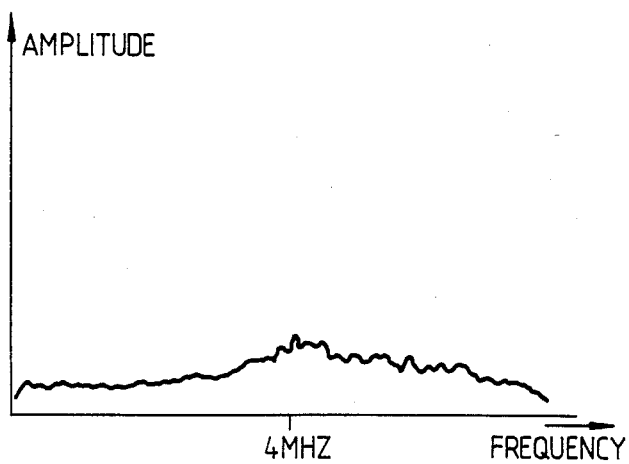

FIG. 13 shows results from a tube having regions of intergranular attack to a nominal depth of 50% of the wall thickness induced by treatment with nitric acid. FIG. 13a shows the response from an unattacked region of the tube. FIG. 13b shows the response from a region having intergranular attack. Observations were made at the 6 MHz resonance. A frequency shift of ~1.9 MHz was observed accompanied by a very considerable broadening of the peak.

An experiment using apparatus as shown in FIG. 4 showed very similar results are obtained from inspection from the inside of the tube.

Figure 14:
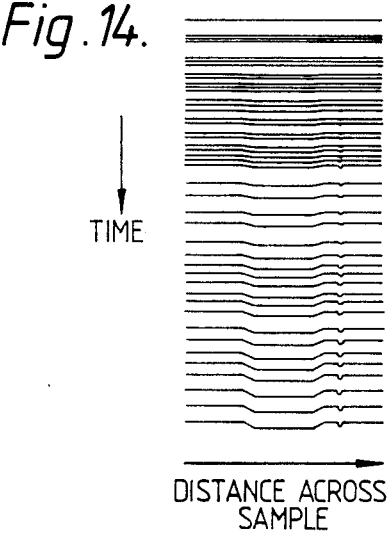
FIG. 14 shows another form of analysis of a sample.

FIG. 14 shows a different form of generation and presentation of the response from a sample, the Figure being a diagrammatic representation of a grey scale image generated from digitised ultrasonic signals. This type of image may be thought of as being built up from a succession of oscilloscope traces of the signal in the following way. Any section through the image from top to bottom is the equivalent of a single oscilloscope trace, with distance from the top of the image being equivalent to the oscilloscope time-base deflection and the brightness of the line representing the y-deflection on the oscilloscope. The direction from left to right on the image represents scanning motion of the ultrasonic transducer over the sample, so that the image displays the changes in signal pattern from different areas of the sample.

FIG. 14 represents the image derived in this way from a scan using compression waves at normal incidence in pulse-echo mode over a region of a sheet of Inconel 600 in which there is a 15 mm wide band of intergranular attack. The image shows that all features of the signal after the first few peaks undergo a slight extra delay in the region where intergranular attack is present, as compared with the unattacked region.

Figure 15:
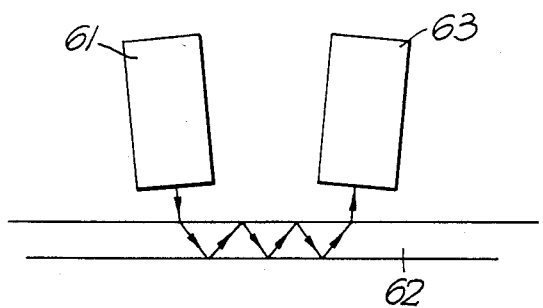
FIG. 15 is a diagrammatic illustration of a further modified form of apparatus.

FIG. 15 shows diagrammatically an alternative technique used for generating images of the form shown in FIG. 14 and referred to as pitch-catch mode, in which pulses from a transmitter transducer 61 enter the sample 62 at an angle to the normal, bounce diagonally between the upper and lower surfaces and are detected by a suitably angled receiver transducer 63.

With this arrangement compression waves undergo partial conversion to shear waves when they are reflected at the sample surfaces and so the signal becomes very complicated with different peaks being affected by the intergranular attack to different extents.

Considering the possible usefulness of an angled probe in an approach based upon frequency analysis as described with reference to FIG. 5, it is noted that at normal incidence only compression waves are transmitted from a standard probe. Above the critical angle for compression waves only shear waves are transmitted, whilst at an angle of incidence between the normal and the critical angle for compression waves, a complex of shear and compression waves are transmitted. While the use of an angled shear wave probe may have certain advantages, the spectrum is broader than that obtained with normal incidence compression waves, partly because the angled probe arrangement limits the number of reflections in the received signal and partly because the shear waves are more strongly attenuated in the intergranular attack region.

The results described indicate that the normal incidence method gives the sharpest spectra and thus the highest sensitivity to peak shifts. However, it appears that there may be more than adequate sensitivity and that the use of angled probes is possible in pitch-catch mode. There is a possibility that the use of shear waves may be desirable for some reason, in which case pitch-catch mode must be used. The choice of transducer configuration for use for inspection in situ of steam generator tubes will also be affected by factors such as the presence of the tube sheet and the change in tube diameter at the point where the expanded region finishes. The apparatus may be used to inspect for other types of defect, simultaneously with the inspection for intergranular attack, and there may then be an advantage in using angled probes and accepting a reduced sensitivity to intergranular attack, in order to improve sensitivity to other defects, such as stress corrosion cracks.

Figure 16:
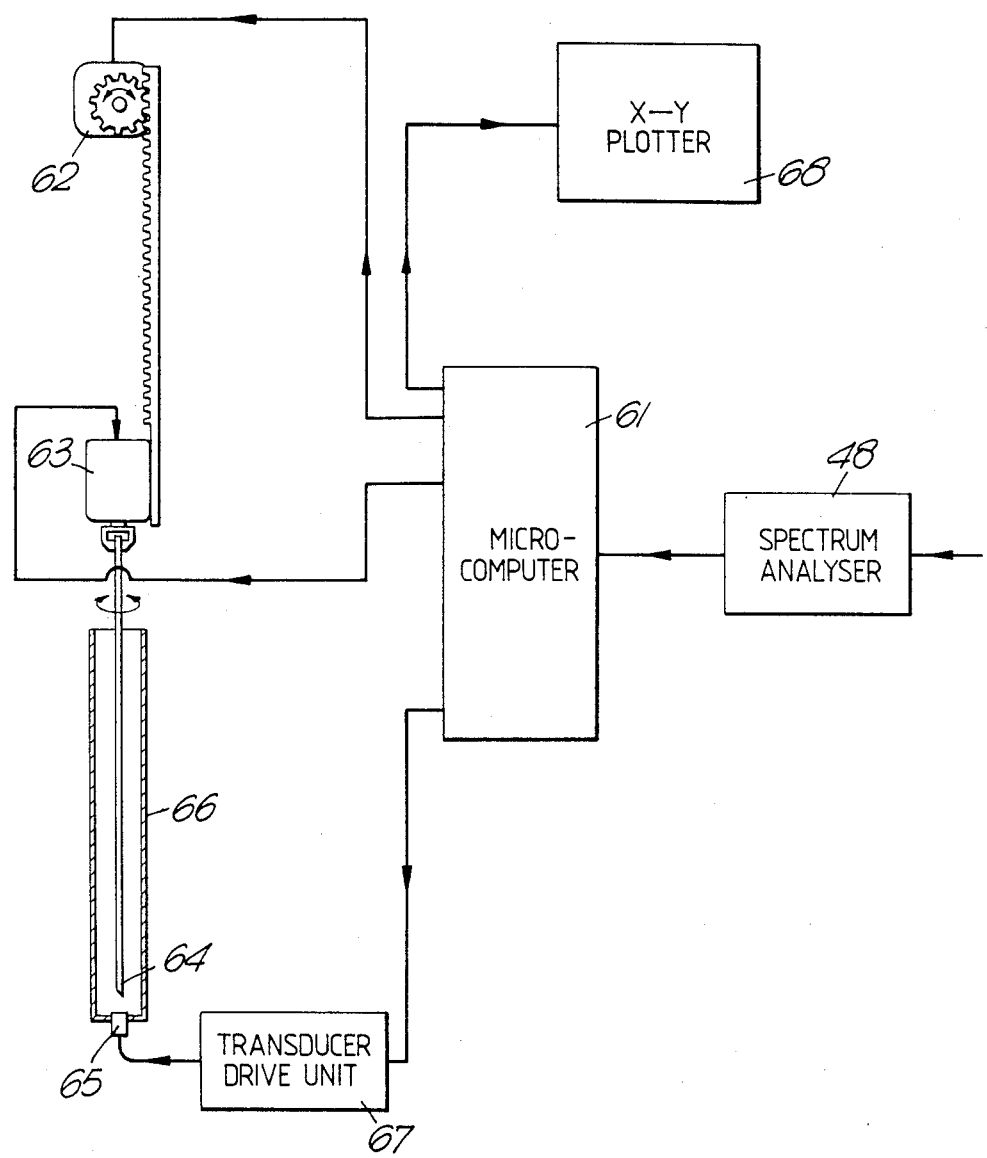
FIG. 16 is a diagrammatic illustration of a development of the apparatus shown in FIGS. 4 and 5.

FIG. 16 illustrates highly diagrammatically an arrangement for automatic inspection of tubes 66.

It has been found in practice that the velocity of sound in the unattacked material of the tubes remains constant to an acceptable level of consistency, but tube bores are eccentric up to about 2.5% of the wall thickness. It is therefore highly desirable to "fingerprint" each tube before it is exposed to inter granular attack.

Referring to FIG. 16, a microcomputer 61 controls motors 62 and 63 which provide respectively for axial and angular movement of rod 64, and drive unit 67 for transducer 65. At three axial positions (top, middle and bottom) of the tube, measurements are taken for four angular positions $\theta = 0$, $\theta = 90°$, $\theta = 180°$, $\theta = 270°$. The resonant frequency at each of these angular positions is detected in the manner described with reference to FIG. 5, the spectrum analyser 48 having a hold feature, such that it is straightforward to pass to the computer 61 the value of the maximum amplitude detected and the frequency at which this occurs.

The computer is programmed to compute and store for each axial position the parameters y, $1/f_m$, $\phi$ where y is the maximum offset due to bore eccentricity expressed as a percentage of tube wall thickness, $f_m$ is the mean of the four resonant frequencies measured at the four angularly spaced locations, and $\phi$ is the angle at which is found the maximum offset due to bore eccentricity.

These sets of stored parameters provide the "fingerprint" record for the tube.

On subsequent test, after the tube has been exposed to intergranular attack, the motors 62, 63 and transducer drive unit 67 are controlled by the computer 61 to perform a programmed sequence of measurements at stepped values of axial position x and angular position $\theta$. From the "fingerprint", the computer calculates the expected resonance frequency $f_o$ assuming no change in tube properties. Where the measured resonance frequency f differs from $f_o$ this is represented by $$s = (1/f - 1/f_o)$$

and s is stored by the computer 61.

Figure 17:
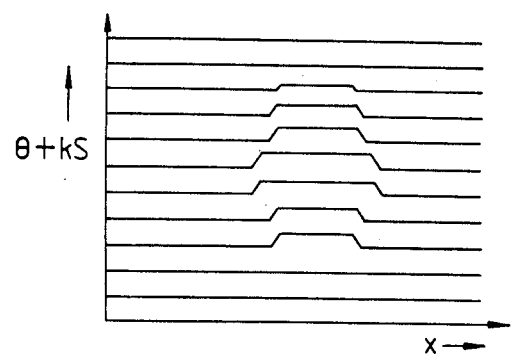
FIG. 17 is a graphical representation of a test result which can be produced using the apparatus of FIG. 16, and FIGS. 18a and 18b show gate functions.

After completion of the test, any selection desired of the stored data can be fed to an X-Y plotter 68. One useful form of presentation is shown in FIG. 17 in which $\theta + ks$ is plotted against x, k being a suitably chosen scaling constant. Where $s = 0$, i.e. no change in the resonant frequency at the measurement position, this yields a series of straight lines parallel to the x axis. The lines are deflected by ks whereever a change in the resonant frequency is detected. The example shown in FIG. 17 illustrates the effect of a narrow band of intergranular attack which has not extended completely around the tube wall.

Figure 18A:
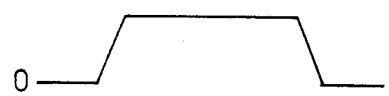
Figure 18B:
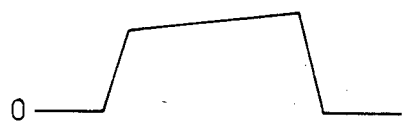

A useful development in the electrical circuit of FIG. 5 is the incorporation of a new form of gate at 46 in which all aspects of the gate signal function can be controlled, i.e. the rate at which it "opens" and "closes" and the gate signal level. FIGS. 18a and 18b give examples. The gating function provided by multiplying the gate signal of form shown in FIG. 18a with the detected and amplified signal on line 47 is, effectively, that of gradual opening and closing of the gate with an intermediate constant "open" state. A gate function of this form has the advantage of reducing the side lobes detected by the specrum analyser, at the expense of slightly broadening the resonance peak.

If a gate function of the form shown in FIG. 18b is used, this is equivalent to sweeping the gain of amplifier 42 during the period the gate is "open". This can be used therefore to replace the ramp generator 49 of FIG. 5.

The invention is not restricted to the details of the foregoing examples. For instance, in the arrangement of FIG. 4, the focused transducer 34a may be replaced with an unfocused transducer and the angled tip of the rod 41 replaced with an conical tip so as to inspect a ring of the tube at one time and determine the fraction of the circumference attacked in an analogous way to that demonstrated for the sheet sample (FIG. 10).

Further it will be appreciated that, for automated inspection, there are many ways in which the detected signals may be handled. Thus, they need not necessarily be visually examined directly on a cathode ray oscilloscope after spectrum analysis or by grey-scale image construction after digitising, they may for example be fed to apparatus set to detect a change in frequency in excess of a predetermined amount and to trigger an alarm in that event.

We claim:

1. A method for detection in a component having thin walls such as a heat exchanger tube of intergranular attack or other forms of corrosion which do not alter significantly the thickness of the said walls, which method comprises injecting ultrasonic elastic wave signals into the walls of the component at a selected plurality of identified locations before the component has been exposed in use to intergranular attack or other corrosion as aforesaid and recording for each location data representative of the resonant frequency with which the signals reverberate across the thickness of the thin walls, injecting ultrasonic elastic wave signals into the component at a selected plurality of locations after the component has been exposed in use to intergranular attack or corrosion as aforesaid, and comparing at each location the resonant frequency with which the signals reverberate within the component with a resonant frequency computed from the recorded data to be that expected for the respective location in the absence of intergranular attack or corrosion.

* * * * *